United States Patent [19]

Donigian

[11] 4,177,672
[45] Dec. 11, 1979

[54] WHISKERING TEST APPARATUS

[75] Inventor: Doulgas W. Donigian, Catonsville, Md.

[73] Assignee: Westvaco Corporation, New York, N.Y.

[21] Appl. No.: 894,106

[22] Filed: Apr. 6, 1978

[51] Int. Cl.$^2$ ............................................ G01N 13/00
[52] U.S. Cl. ............................. 73/150 R; 73/432 SD; 101/170
[58] Field of Search ............... 101/DIG. 13, 426, 219, 101/170, 153, 163; 118/621, 623, 624, 625, 626, 659, 660; 346/153, 158, 159; 401/143, 265; 73/472 SD, 150 R

[56] References Cited

U.S. PATENT DOCUMENTS

| | | | |
|---|---|---|---|
| 1,665,099 | 4/1928 | Kiesling et al. | 101/407 BP |
| 1,865,610 | 7/1932 | Blair | 101/DIG. 13 |
| 2,143,376 | 1/1939 | Hansell | 346/153 X |
| 2,173,741 | 9/1939 | Wise et al. | 401/143 X |
| 2,558,900 | 7/1951 | Hooper | 101/219 |
| 2,748,018 | 5/1956 | Miller | 346/153 X |
| 3,052,213 | 9/1962 | Schaffert | 118/659 X |
| 3,661,081 | 5/1972 | Wright | 101/DIG. 13 |
| 3,810,193 | 5/1974 | Metcalfe et al. | 346/153 |
| 3,921,179 | 11/1975 | Weerstra | 346/153 |

OTHER PUBLICATIONS

Gravure Research Institute-Press Report, No. P-23, Oct. 1966, "Electrostatic Transfer of Ink in Gravure Printing" Gravure Research Institute, Inc., 22 Manhasset Ave, L.I., N.Y.
American Ink Maker-Feb. 1974, pp. 24, 26, 27, 48, 49.
Gravure Research Institute-GRI Newsletter, No. 29, Sep. 1973, pp. 17-21.
Gravure Research Institute-Research Report No. M-53, Nov. 1975-"Whiskering in Gravure Printing".
Gravure Research Institute-GRI Newsletter, No. 34, Jun. 1976, pp. 40-44.

*Primary Examiner*—J. Reed Fisher

[57] ABSTRACT

A means is disclosed for producing whiskers with a laboratory apparatus that simulates an electrostatically assisted gravure press. The apparatus does not employ the dynamic printing conditions normally found on a printing press, but utilizes static conditions to reproduceably generate whiskers as a means for assessing the whiskering tendency of the ink or paper involved.

1 Claim, 1 Drawing Figure

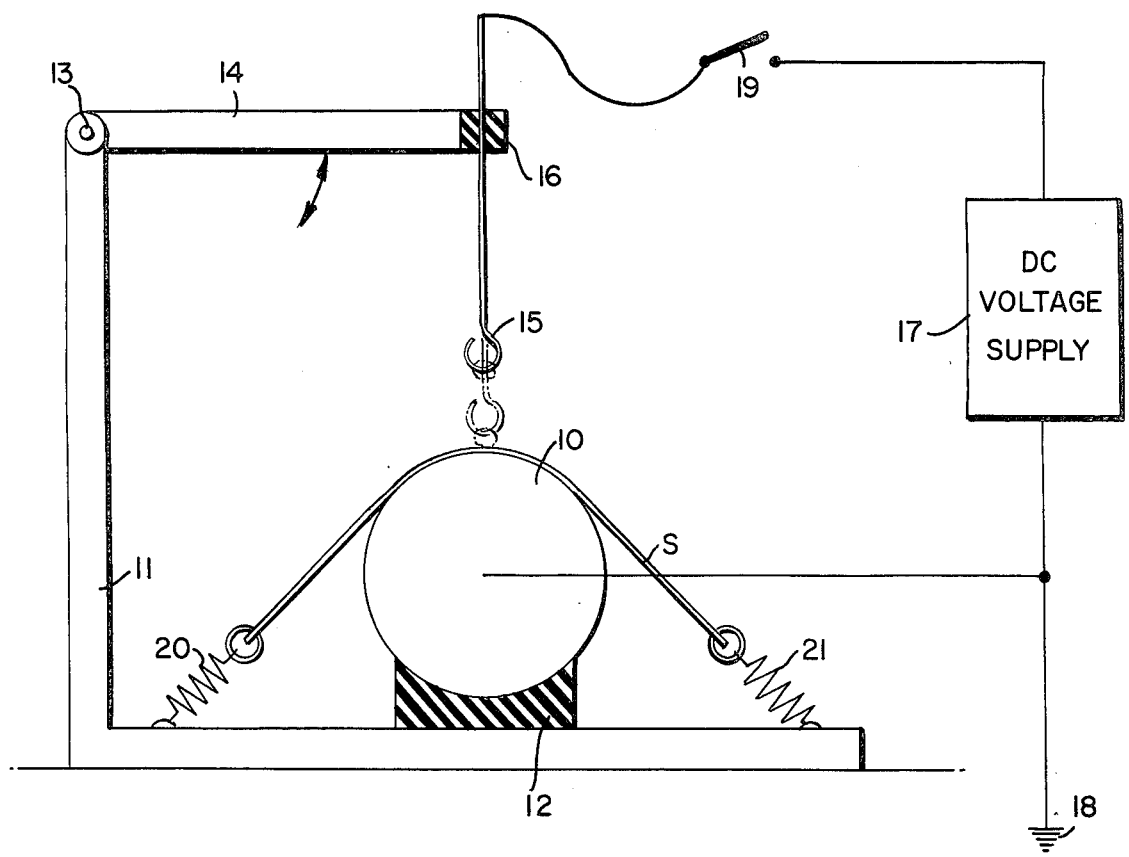

WHISKERING TEST APPARATUS

BACKGROUND OF INVENTION

Gravure printing is becoming increasingly popular and has been described as the printing process of the 80's. One of the most attractive features of gravure printing is the ability to produce prints having uniform tonal gradations in the highlight and middle tone areas. This continuous tone effect makes the gravure process ideal for high quality printing. However, where the printing substrates are ink repellent, or hard, coarse, grainy papers, grainy printing or dot skipping can be a problem. To combat this problem, electroassist is often used on gravure presses to insure a complete transfer of the ink from the gravure cells to the substrate. The primary function of electroassist is to improve the ink transfer to the lighter tone areas on a printed substrate that normally would not accept the ink. Electroassist is carried out by producing an electric field in the printing nip which deforms the surface of the ink in individual gravure cells and increases the likelihood of contact between the ink and the substrate. Unfortunately, the electric forces generated in the nip on the ink continue to act on the transferred ink as the printed substrate leaves the nip. Thus, if the transferred ink is not immediately dried or otherwise immobilized these forces may cause the ink to spread beyond its proper boundaries. The latter phenomena is defined as whiskering, or the rough edged spreading of ink due to electrical forces on the ink. Accordingly, in order to study the whiskering phenomena under controlled laboratory conditions, the present invention was developed as a test device for reproduceably producing whiskers to measure the whiskering tendency of different substrates and inks.

SUMMARY OF INVENTION

The present invention comprises a laboratory apparatus for simulating an electroassisted gravure printing process. The laboratory apparatus of the present invention consists of only the most basic elements necessary to produce such a system, including a conductive, grounded backing element analogous to the impression roll of a gravure press, a stylus element that may be raised to a potential analogous to the gravure printing cylinder of a gravure press, and, a DC power source with adjustable voltage connected between the backing element and stylus, all mounted on a suitable frame. Only the stylus is arranged to be movable because it is not necessary to simulate the dynamic conditions experienced with a printing press in order to produce whiskers. The latter conclusion is believed to be sound in view of the mechanism for whiskering on which the present invention is based, i.e., the movement of a weakly conductive liquid (ink) on an insulator (paper) in the electric field produced by the applied electroassist voltage. This mechanism is generally contrary to at least one widely accepted explanation for the whiskering phenomena. The latter explanation holds that whiskering is produced by a filamentation effect, or the mechanical stretching of the ink into filaments between the gravure cylinder and printed substrate, during ink split beyond the printing nip. Before the ink split is complete, the ink may be stretched for some distance creating filaments, and the filaments, when they finally break, tend to fall onto unprinted areas producing the whiskering effect. However, independent observations with stop action photography on a commercial printing press demonstrated that whiskering does not begin until after the printed substrate leaves the nip. Thus, the design of the laboratory apparatus of the present invention is based on the aforementioned mechanism, i.e., the presence of electrical forces or a trapped charge on the transferred ink due to the electrostatic assist.

In operation, the apparatus is used as follows: a sample printing substrate is placed on the backing plate, a drop of ink is placed on the stylus, the stylus is lowered until it touches the substrate (to simulate the printing step), a voltage is applied to the circuit (to simulate the electroassist step), the stylus is lifted from the substrate and the voltage removed. Under laboratory conditions, the above described apparatus when used as set forth will produce whiskers around the periphery of the transferred ink drop. Moreover, as disclosed hereinafter, whiskers produced in a commercial printing trial were found to be substantially equivalent to whiskers produced on samples of the same printing substrate using the test apparatus of the present invention.

DESCRIPTION OF DRAWING

The FIGURE of drawing discloses a schematic representation of a typical laboratory whiskering producing apparatus according to the present invention.

DETAILED DESCRIPTION

The whiskering test apparatus shown schematically in the accompanying FIGURE of drawing comprises a conductive backing cylinder 10 mounted on a frame 11 by an insulated block 12. The backing element 10 does not have to be cylindrical but could take any desired form such as a plate element of circular or rectangular shape. The cylindrical shape chosen has the advantage that it most nearly corresponds to the impression roll of a typical gravure press, and the cylindrical shape permits sample substrates to conform to the backing member substantially as would occur on a press. The frame 11 includes at the top thereof a pivot pin 13 to which is attached an arm 14 for mounting the printing stylus 15. Stylus 15 is insulated from the arm 14 and frame 11 by an insulated block 16. The test apparatus is completed with the addition of a DC power supply 17 adjustable from 0-2500 volts, that is connected between the printing stylus 15 and the backing cylinder 10 with the backing cylinder connected to ground at 18. A switch 19 is included in the circuit for raising the stylus to the desired potential for electroassist.

In use, a sample S of paper or the like is placed on the backing cylinder 10 and held in place by any suitable devices such as the spring elements 20,21. With switch 19 open, a drop of ink is placed on stylus 15 and arm 14 is rotated to bring the stylus into contact with paper sample S. This action simulates the printing step. In order to produce the whiskering phenomena, the switch 19 is closed to energize the circuit. If the apparatus and paper sample S are kept at sufficiently low relative humidity (below 25% RH is adequate), and certain inks and papers are used, a potential of sufficient voltage will cause the formation of whiskers around the surface of the transferred ink drop. Neither the stylus nor any other part of the apparatus is moved during the formation of the whiskers.

The whiskering of the ink under the conditions set forth above is believed to be due to the movement of a weakly conductive liquid (ink) on an insulator (paper) in the electric field produced by the voltage source 17.

The electric forces act on the ink through two mechanisms. First, there is the net charge attraction. If the ink retains an excess positive or negative charge, it will experience a net force in the electric field because of this charge. Secondly, there are the forces produced as a result of polarization of a neutral liquid. However, the latter forces are not believed to be of major importance in the whiskering phenomena with the test apparatus disclosed for several reasons. First, the tendency of inks to whisker has been found to be not dependent on their dielectric constant, and polarization forces are generally dependent on the dielectric constant of the liquid involved. Secondly, a force is exerted on the paper by the ink when the potential is applied. This force makes it harder to lift the paper away from the conductive backing cylinder 10. Moreover, this force persists even after the potential is shut off and the stylus is removed. A force dependent on polarization of a liquid at room temperature would be expected to decay much more rapidly after removal of the potential. And, thirdly, whiskering does not occur unless there is electrical contact between the stylus and ink. Polarization effects should not require contact since they result from the electric field and not a flow and accumulation of charge. Thus, the primary force which results in whiskering arises from the interaction between the net mobile charge on the surface of the ink and the electric fields around the ink.

For instance, when the ink deposited on paper sample S is charged with the applied voltage source 17, the ink acts as one plate of a capacitor, the other plate being the conductive backing cylinder 10, and the paper sample S serves as the capacitor dielectric. As the charge accumulates on the paper/ink interface, the ink is subjected to a spreading force dependent on the electric field developed by the charge and the dielectric constant of the paper sample. When this force exceeds the restraining forces of surface tension and viscous drag, spreading of the deposited ink begins. If the paper sample S is lifted from the conductive backing cylinder 10 after removal of the potential, any whiskering tendency of the ink is magnified due to the mutual repulsion of net charge trapped on the ink under increasing voltage, i.e., as the inked sample with its trapped charge is removed from the conductive backing cylinder 10, the capacitance of the system decreases producing an increase in voltage.

Factors which influence whiskering as determined by the whiskering test apparatus of the present invention are as follows. The voltage applied between the stylus and conductive backing is important. No whiskering, severe whiskering or any intermediate amount can be produced according to the amount of voltage applied. The effect of the composition of the substrate tends to affect the ability of the substrate to stop whiskering rather than the ability to cause whiskering. For example, the porosity of the paper sample may be such as to remove solvent from the ink and help to immobilize the ink and prevent spreading. The surface resistivity of the substrate is another important factor which influences whiskering. A general rule of thumb is that at about 900 volts, very little whiskering occurs on paper having a surface resistivity lower than about $7 \times 10^{12}$ ohms. Meanwhile, the properties of the liquid ink such as conductivity, dielectric constant, surface tension and viscosity also play a role in the production of whiskers. However, of these four properties, only conductivity plays a major role. Similarly, while the polarity of the applied DC voltage would appear to influence whiskering, there is no clear evidence of such influence with the test apparatus. In the commercial printing operation this same result may be due to the fact that the potential generated in the nip arises from two sources, i.e., the applied ESA (Electrostatic assist) voltage and static electricity due to the traveling motion of the web or sheets and friction between the moving parts. In some cases these potentials may reinforce one another whereas in other cases they may counteract each other. Finally, in both commercial practice and with the test apparatus, the effect of the printing environment plays a major role in whiskering. Experience has shown that at 50% RH or greater, whiskering is minimal or nonexistent. Similarly it has been found that more whiskering occurs in the winter than in the summer, while paper with a moisture content greater than about 6% rarely whiskers.

In order to compare the results obtained with the laboratory test apparatus disclosed herein and the performance of a commercial operation, unprinted samples of paper from a commercial trial were used as substrates on the test apparatus. Several types of paper were printed at the trial and ranked subjectively according to the severity of whiskering. Samples of these same papers were then tested using the apparatus disclosed hereinbefore and given a subjective ranking for comparison with the ranking of the commercial papers. The results are shown in Table I.

Table I

Comparison of Laboratory and Commercial Press Whiskering

| Sample | Laboratory Test (Rank) | Commercial Trial (Rank) |
|---|---|---|
| 1 | Very Severe (1) | Severe-Worst (1) |
| 2 | Severe-Intermediate (2) | Severe (2.5) |
| 3 | Severe-Intermediate (3) | Severe-Intermediate (4) |
| 4 | Intermediate (4) | Severe (2.5) |
| 5 | Intermediate (5) | Severe-Intermediate (5) |
| 6 | Intermediate slight (6) | Slight (6) |
| 7 | Very Slight (7) | None (7) |

The laboratory Test samples were conditioned to 20% RH and applied with 900 volts using a 10 centipoise standard ink. The commercial trial was conducted under prevailing ambient conditions using an applied voltage of about 400 volts to the ESA unit with a standard ink of about 10 centipoise. Since the paper went through the normal sequences of printing and drying on the commercial press, the actual condition of the paper surface when printed could not be readily determined. However, it will be noted that the results shown in Table I demonstrate a good working correlation between the whiskering produced with the laboratory test apparatus and that experienced on the commercial press. Other tests showed that both the laboratory test apparatus and the commercial printing operation respond similarly to the same variables. That is, whiskering is reduced in both instances by an increase in paper conductivity or an increase in the RH of the environment. Likewise, as ink conductivity is increased, whiskering is reduced in both cases. Meanwhile, as the ESA voltage is increased both on the press and on the laboratory apparatus, whiskering becomes more severe. Finally, in each case, the whiskers produced look very much alike.

Accordingly, it may be seen that the present invention fully discloses a useful tool for determining the whiskering tendency of paper or ink with a laboratory device that simulates an electroassisted gravure printing press. Moreover, the apparatus disclosed may be seen to produce whiskers similar to those actually encountered on a commercial press without duplicating the dynamic conditions found on the press. Accordingly, it is desired, therefore, not to limit the invention except as defined in the claims set forth below, since, from the above description, it will be apparent to those skilled in the art that the invention is capable of numerous modifications.

I claim:

1. An apparatus for producing the whiskers associated with an electroassisted gravure printing process under static conditions without employing the dynamic printing conditions of an electroassisted gravure printing process comprising, a frame element, a conductive, grounded backing member mounted on said frame element, means for insulating said grounded backing member from said frame element, a pivotally adjustable arm member mounted on said frame element, a printing stylus connected to said arm member and arranged to lie normally in spaced relation from said backing plate, means for insulating said printing stylus from said arm member, and a DC power supply connected to said printing stylus, said power source being adapted to produce an electric field between said backing member and printing stylus after a drop of ink placed on said stylus is transferred to a printing substrate which is releasably attached in fixed relation on said backing member.

* * * * *